(12) United States Patent
Kim et al.

(10) Patent No.: US 9,326,960 B2
(45) Date of Patent: May 3, 2016

(54) COMPOSITION FOR PREVENTING OR TREATING EYE DISEASES, CONTAINING S-ALLYL-L-CYSTEINE AS ACTIVE INGREDIENT, AND PHARMACEUTICAL FORMULATION CONTAINING SAME

(71) Applicant: PHARMAKING CO., LTD., Chungcheongbuk-do (KR)

(72) Inventors: Soon Bae Kim, Gyeonggi-do (KR); Gwang Soon Kim, Gyeonggi-do (KR); Wan Bae Kim, Seoul (KR); Wie Jong Kwak, Seoul (KR); Sun Duck Jeon, Seoul (KR); Hyung Young Yoon, Seoul (KR); Young Pyo Jang, Seoul (KR)

(73) Assignee: PHARMAKING CO., LTD., Chungcheongbuk-do (KR)

( * ) Notice: Subject to any disclaimer, the term of this patent is extended or adjusted under 35 U.S.C. 154(b) by 0 days.

(21) Appl. No.: 14/422,110

(22) PCT Filed: Aug. 19, 2013

(86) PCT No.: PCT/KR2013/007420
§ 371 (c)(1),
(2) Date: Feb. 17, 2015

(87) PCT Pub. No.: WO2014/027865
PCT Pub. Date: Feb. 20, 2014

(65) Prior Publication Data
US 2015/0231100 A1    Aug. 20, 2015

(30) Foreign Application Priority Data
Aug. 17, 2012  (KR) ........................ 10-2012-0089857

(51) Int. Cl.
*A61K 31/195*  (2006.01)
*A61K 36/8962*  (2006.01)
*A61K 45/06*  (2006.01)

(52) U.S. Cl.
CPC ............ *A61K 31/195* (2013.01); *A61K 36/8962* (2013.01); *A61K 45/06* (2013.01)

(58) Field of Classification Search
CPC .................................................... A61K 31/195
USPC ........................................................ 514/562
See application file for complete search history.

(56) References Cited

FOREIGN PATENT DOCUMENTS

WO   2005-077176 A1   8/2005

OTHER PUBLICATIONS

International Search Report for PCT/KR2013/007420, Dec. 17, 2013.
Chen, Yan-Qing et al., The Effects and Underlying Mechanisms of S-Allyl L-Cysteine Treatment of the Retina After Ischemia/Reperfusion, Journal of Ocular Pharmacology and Therapeutics, vol. 28, No. 2, pp. 110-117, Apr. 2, 2012.
Ahamad, M. S. et al., Aged garlic extract and S-allyl cysteine prevent formation of advanced glycation endproducts, European Journal of Pharmacology, vol. 561, pp. 32-38, 2007.
Hung, L Y., The Antioxidant Properties of Garlic Compounds: Allyl Cysteine, Alliin, Allicin, and Allyl Disulfide, Journal of Medicinal Food, vol. 9, No. 2, pp. 205-213, 2006.
Ismael, A. A. et al., Efficacy of Aqueous Garlic Extract on Growth, Aflatoxin B1 Production, and Cyto-Morphological Aberrations of Aspergillus Flavus, Causing Human Ophthalmic Infection: Topical Treatment of A. Flavus Keratitis, Brazilian Journal of Microbiology, vol. 43, No. 4, pp. 1355-1364, 2012.

*Primary Examiner* — Taofiq A Solola
(74) *Attorney, Agent, or Firm* — The PL Law Group, PLLC

(57) ABSTRACT

Disclosed is a composition for preventing or treating eye diseases. The composition for preventing or treating eye diseases contains S-allyl-L-cysteine, a pharmaceutically acceptable salt thereof, or a solvate or a hydrate thereof as an active ingredient, and may inhibit photo-oxidation. The composition for preventing or treating eye diseases inhibits the accumulation of A2E in retinal pigment epithelial cells and the oxidation of A2E, thereby remarkably preventing or treating eye diseases including age-related macular degeneration or degenerative retinal disorder.

8 Claims, 2 Drawing Sheets

COMPOSITION FOR PREVENTING OR TREATING EYE DISEASES, CONTAINING S-ALLYL-L-CYSTEINE AS ACTIVE INGREDIENT, AND PHARMACEUTICAL FORMULATION CONTAINING SAME

CROSS REFERENCE TO RELATED APPLICATIONS AND CLAIM OF PRIORITY

This patent application is a National Stage entry from International Application No. PCT/KR2013/007420, filed Aug. 19, 2013, which claims priority to Korean Patent Application No. 10-2012-0089857, filed Aug. 17, 2012, entire contents of which are incorporated herein by reference.

BACKGROUND

1. Field

The present invention relates to a composition for the prevention or treatment of eye diseases. More particularly, the present invention relates to a composition comprising S-allyl-L-cysteine as an active ingredient useful for preventing or treating eye diseases.

2. Description of the Related Art

The macula or macula lutea is a nerve tissue positioned near the center of the retina of the human eye, and is highly responsible for the vision of the eye because it is the center of the visual field where images fall, and it is where most visual cells are concentrated. Macular degeneration (MD), caused by various factors, is a medical condition that results in visual impairment. Macular degeneration is one of the three leading causes of irreversible blindness, together with glaucoma, and diabetic retinopathy.

Macular degeneration occurs largely in dry and wet forms. Dry macular degeneration is a major cause of blindness and visual impairment in older adults. The dry form of macular degeneration leads to atrophy of the retinal pigment epithelial layer below the retina, which causes vision loss through loss of photoreceptors (rods and cones) in the central part of the eye. In wet macular degeneration, which accounts for much fewer diagnosed cases than those of the dry form, abnormal blood vessel growth can form beneath the macula; these vessels can leak blood and fluid into the macula and damage photoreceptor cells. Caused by vessels, hemorrhage, fluid, and scarring, the wet form of macular degeneration can progress rapidly and over time cause severe damage to central vision.

Age-related macular degeneration (AMD), although its etiology is yet unknown, is known to exhibit the age-associated, excessive accumulation of pigment in retinal pigment epithelial (RPE) cells in its early stages. Representative among pigment deposits in RPE cells is N-retinylidene-N-retinyl-ethanolamine (A2E), which is synthesized by conjugating all-trans retinal with ethanolamine. A2E accumulates in RPE cells of the eye, and generates singlet oxygen upon photoexcitation, which leads to an oxidation-associated loss of double bond conjugation, causing damage to RPE cells.

To date, a complete therapy for age-related macular degeneration is difficult to expect mainly because the exact mechanism of macular degeneration is still unknown. It is thus important to appropriately prevent or minimize vision loss caused by the progress of macular degeneration. Recent discoveries have applied antioxidant vitamins and zinc (Zn) to the therapy of age-related macular degeneration because of their ability to prevent the progression of macular degeneration. For the wet form of age-related macular degeneration, early laser treatment can reverse the formation of new blood vessels, thus preventing aggravation of the disease. However, these therapies do not yet guarantee satisfactory results. Currently, prophylaxis is most important in treating age-related macular degeneration.

The accumulation of lipofuscin, which is the name given to lipid-containing, finely granular yellow-brown pigment granules in retinal pigment epithelial cells is known to closely correlate with the onset of atrophic macular degeneration that accounts for a significant portion of diagnosed age-related macular degeneration cases, as demonstrated by many studies.

According to day-to-day variations in life, retinal pigment epithelial cells digest optic discs of photoreceptors of rod cells in the daytime, and optic discs of photoreceptors of cone cells at night, with concomitant production of lipofuscin as a residue of lysosomal digestion. In addition, retinal pigment epithelial cells phagocytizes adjacent, dysfunctional retinal pigment epithelial cells and photoreceptors, which adds to the load of lipofuscin accumulation. Lipofuscin is composed mainly of non-degradable, bis-retinoid adducts and is produced via the following biosynthesis pathway: 1) photoreceptor cells, which absorb light in the retina, produce vitamin A aldehyde (all-trans-retinal) from 11-cis-retinal by photoisomerization; 2) the all-trans-retinal is transferred from the photoreceptors to retinal pigment epithelium where it is converted into a lipofuscin fluorophore by a series of condensation reactions. The lipofuscin fluorophore mediates light-dependent lipid peroxidation, which may damage retinal cells, resulting in a loss of vision, and even blindness. Lipofuscin fluorophore is generated mainly in postmitotic cells (e.g., cardiomuscular cells, neurons, retinal epithelial cells, etc.) where active metabolism occurs. Examples of the lipofuscin fluorophore isolated thus far include A2E and a double bond isomer thereof, Iso-A2E, and an all-trans-retinal dimer conjugate (atRAL dimer).

All of these compounds are generated by phosphate hydrolysis of phosphatidylpyridinium bisretinoid (A2PE), which is generated via the condensation of all-trans-retina and phosphatidylethanolamine, both isolated from the visual cycle. One molecule of all-trans-retinal reacts with phosphatidylethanolamine (PE) to generate the Schiff base N-retinylidene-phosphatidylethanolamine (NRPE), which is found to be a substrate for the photoreceptor-specific ATP-binding cassette transporter ABCA4. NRPE from the normal visual cycle is associated with another molecule of all-trans-retinal to generate A2PE, which is promoted under certain environments, intense light, or oxidative stress (Sparrow et al., Vision Res, 2003. 43(28): 2983-90).

According to a variety of studies, A2E accumulation increases with age, and the compounds undergo singlet oxygen-mediated photo-oxidation under intense light. Also, the photo-oxidative product of A2E was found to be a main factor of age-related macular degeneration that is causative of inflammation, as assayed by immune complementation.

The macular degeneration medication market is divided largely into medicines and health functional foods. In South Korea, Ranibizumab (Lucentis) is the only medicine that is approved and on the market as a therapeutic agent for wet macular degeneration. However, at present there are no therapeutic agents approved to treat dry macular degeneration. Ranibizumab is a humanized monoclonal antibody that recognizes and blocks vascular endothelial growth factor (VEGF) A for neovascular age-related macular degeneration so that vision lowered by wet macular degeneration may be recovered, or is not degraded further. According to clinical trials, however, Genentech warned that Ranibizumab may increase the risk of stroke occurrence. In addition, Ranibizumab is expensive, and is marketed as an intraocular injection that is inconvenient for administration.

Turning to the health functional food field, lutein is solely approved as an individual type. Lutein, which accumulates in the retina, serves as a photoprotectant for the macula leutea from degeneration by maintaining macular pigment levels. However, some research has shown that the long-term use of a supplement containing carotenoid, such as lutein, increases the risk of the onset of lung cancer, particularly in smokers. Hence, it may be dangerous for patients who smoke tobacco to ingest lutein-related products.

In addition, although not approved as functional materials by the KFDA, natural products known to have therapeutic effects on macular degeneration include zeaxanthin, a macular pigment like lutein, and anthocyanins, abundantly found in berries. However, there are insufficient studies on the effect of these compounds on macular degeneration. In recent years, the occurrence of macular degeneration has increased in middle-aged, as well as elderly people, while therapeutic modalities for macular degeneration are sparse. Therefore, there is an urgent need for the development of medicines and health functional foods that are useful for preventing macular degeneration.

Similarly, garlic, belonging to the *Allium* genus, has attracted keen attention as a natural material because it is known to have antibacterial, antifungal, anti-oxidative, and anticancer activity (Ankri et al., Microbes Infect. 1(2), pp 125-129, 1999). Further, garlic has been shown to effectively prevent thrombosis, inflammation, and oxidative stress (Sener et al., Mol Nutr Food Res., 51(11), pp 1345-1352, 2007). Garlic contains a variety of ingredients including non-sulfur compounds and organosulfur compounds among which are steroid saponins such as eruboside-B that exhibit antifungal and anticancer effects (Matsuura H et al., ChemPharm Bull (Tokyo), 36: 3659-3663, 1988), glycoside fractions that function to lower cholesterol levels (Slowing et al., J Nutr., 131, pp 994S-9S, 2001), and beta-chlorogenin that inhibits platelet aggregation (Rahman K et al., J. Nutr. 2006).

As a natural constituent of mature garlic, S-allyl-L-cysteine is reported to exhibit various pharmaceutical efficacies including a suppressive effect on arteriosclerosis due to its antioxidant activity, and an inhibitory effect on some cancer cell lines (Proceedings of the American Association for Cancer Research, 30, p 181, 1989).

S-Allyl-L-cysteine significantly recovered damaged hepatocytes as assayed in rat models of carbon tetrachloride-induced liver injury (CHOI, Soo Yeon, 2009, Effects of S-Allyl Cysteine on carbon tetrachloride-induced liver injury in rats). Further, S-Allyl-L-cysteine also protects the stomach against *Helicobacter pylori* (Bang, Sung Hye, 2010, Protective effect of S-allyl-L-cysteine (SAC) on *Helicobacter pylori*-infected mice).

In Korean Patent Application Unexamined Publication No. 10-2011-0032641 (titled "Composition for preventing or treating gastrointestinal disorders comprising s-allyl-l-cysteine as an active ingredient"), it is disclosed that S-allyl-L-cysteine can suppress the infection of *Helicobacter* and protect the stomach from *Helicobacter*-induced damage.

This application may reference various publications by author, citation, and/or L by patent number, including without limitation, articles, presentations, and patents. The disclosures of each of any such references in their entireties are hereby incorporated by reference into this application. However, nowhere is the preventive and therapeutic effect of S-allyl-L-cysteine on age-related macular degeneration mentioned in the articles and patent documents.

Currently, it would be medically difficult to expect a perfect cure for age-related macular degeneration, and therefore, prevention is most important. As disclosed, intensive and thorough research conducted by the present inventors has resulted in the finding that S-allyl-L-cysteine is effectively preventive and curative of age-related macular degeneration.

SUMMARY

In one embodiment, provided is a pharmaceutical composition for the prevention or treatment of photo-oxidation-induced eye diseases, including S-allyl-L-cysteine, a derivative thereof, or a pharmaceutically acceptable salt thereof as an active ingredient. The pharmaceutical composition may inhibit the accumulation of A2E in retinal pigment epithelial cells and suppress the photo-oxidation of A2E, thus eliminating the etiology of the eye diseases.

In another embodiment, provided is a medicinal formulation prepared from the composition for the prevention or treatment of eye diseases.

As disclosed, an aspect of the present invention provides a pharmaceutical composition for the prevention or treatment of eye disease, the composition including S-allyl-L-cysteine, a pharmaceutically acceptable salt thereof, or a solvate or hydrate thereof as an active ingredient, and exhibiting inhibitory activity against photo-oxidation.

The pharmaceutical composition for the prevention or treatment of eye disease includes S-allyl-L-cysteine, a pharmaceutically acceptable salt thereof, or a solvate or hydrate thereof as an active ingredient, and may inhibit the oxidation of N-retinylidene-N-retinyl-ethanolamine (A2E) in retinal pigment epithelial cells.

The eye diseases may be age-related macular degeneration or degenerative retinal disorders.

The pharmaceutical composition for the prevention or treatment of eye disease may contain S-allyl-L-cysteine in an amount of 5 to 99.9% by weight.

In the composition for the prevention or treatment of eye disease, S-allyl-L-cysteine may be obtained by isolation and purification from the plant *Allium* genus, by synthesis, or by fermentation.

The composition for the prevention or treatment of eye disease may further include an anti-inflammatory agent or an anti-oxidant agent.

In the composition for the prevention or treatment of eye disease, the anti-inflammatory agent may be selected from the group consisting of ibuprofen, ketoprofen, flurbiprofen, fenoprofen, naproxen, piroxicam, tenoxicam, isoxicam, melo-xicam, indomethacin, aceclofenac, diclofenac, and a combination thereof, and the anti-oxidant agent may be selected from the group consisting of vitamin A, vitamin C, vitamin E, carotenoid, zinc, copper, iron, manganese, lutein, zeaxanthin, selenium, glutathione (GSH), lycopene, and a combination thereof.

Contemplated in accordance with another aspect of the present invention is a medicinal formulation, including the composition for the prevention or treatment of eye disease, the medicinal formulation being selected from the group consisting of an oral dosage form, a mucosal application, an injection, an inhaler, and an external application.

DETAILED DESCRIPTION

Figure 1:
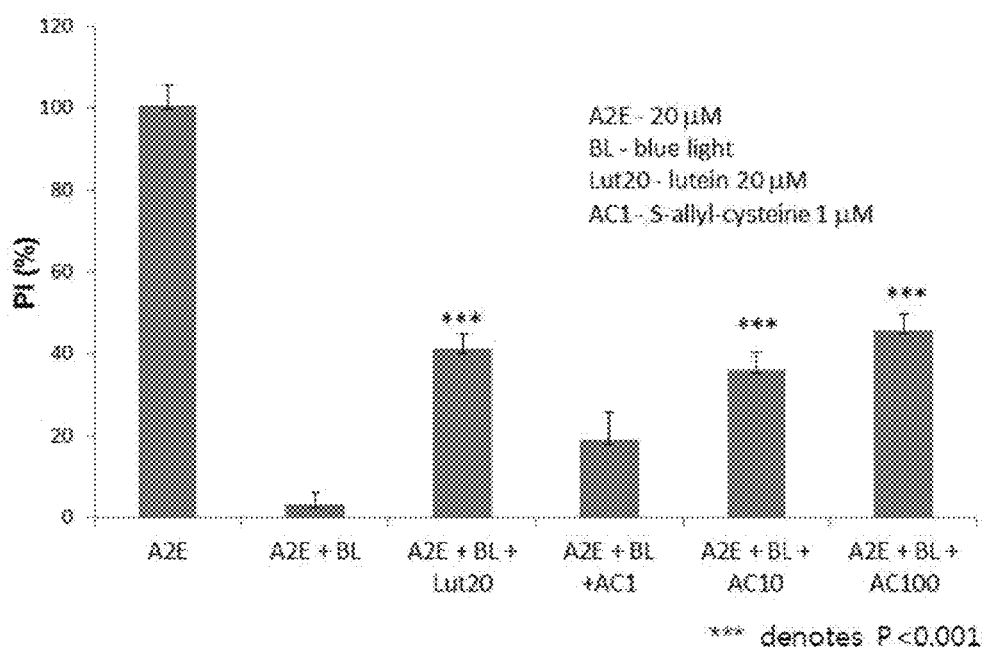
FIG. 1 is a graph showing the inhibitory activity of S-allyl-cysteine against photo-oxidation.

In accordance with an aspect thereof, the present invention addresses a pharmaceutical composition for the prevention or treatment of eye disease, the composition including S-allyl-L-cysteine, a pharmaceutically acceptable salt thereof, or a solvate or hydrate thereof as an active ingredient, and exhibiting inhibitory activity against photo-oxidation.

The pharmaceutical composition for the prevention or treatment of eye disease includes S-allyl-L-cysteine, a pharmaceutically acceptable salt thereof, or a solvate or hydrate thereof as an active ingredient, and may inhibit the oxidation of N-retinylidene-N-retinyl-ethanolamine (A2E) in retinal pigment epithelial cells.

As a natural constituent of mature garlic, S-allyl-L-cysteine is reported to exhibit various pharmaceutical efficacies including a suppressive effect on arteriosclerosis due to its antioxidant activity, and an inhibitory effect on some cancer cell lines (Proceedings of the American Association for Cancer Research, 30, p 181, 1989).

As mentioned above, the composition for the prevention or treatment of eye disease may include a pharmaceutically acceptable salt of S-allyl-L-cysteine as an active ingredient, effectively preventive and curative of macular degeneration. It may be an acid addition salt or a quaternary ammonium salt. Examples of the acid addition salt include inorganic acid salts such as hydrochloride, hydrobromide, hydroiodide, sulfate, phosphate, etc., and organic acid salts such as oxalate, maleate, fumarate, lactate, malate, succinate, tartarate, benzoate, methanesulfonate, etc., but are not limited thereto. Examples of the quaternary ammonium salts may include, but are not limited to, lower alkylhalogenides such as methyl iodide, methyl bromide, ethyl iodide, ethyl bromide, and the like; lower alkyl sulfonate such as methylmethane sulfonate, ethylmethane sulfonate, and the like; and lower alkyl acrylsulfonate, such as methyl-p-toluene sulfonate.

In addition, because S-allyl-L-cysteine or a pharmaceutically acceptable salt thereof may be in the form of solvates or hydrates, the composition of the present invention may utilize a solvate or hydrate of S-allyl-L-cysteine or the pharmaceutically acceptable salt as an active ingredient.

As used herein, the term "pharmaceutically acceptable derivative" refers to a compound that is derived by substituting an atom or an atomic group for a portion of the mother compound, without altering the fundamental structure, as exemplified by a methyl derivative or a chloride derivative. Various derivatives synthesized from a fundamental structure may lead to more potent pharmaceutical efficacy than that of the mother compound.

A derivative of S-allyl-L-cysteine can be readily prepared using a method known in the art (e.g., Burger's Medicinal Chemistry and Drug Chemistry, 5th ed., 1:172-178 and 949-982(1995)).

The eye disease may be age-related macular degeneration, or a degenerative retinal disorder.

Macular degeneration (MD) is a medical condition that results in a loss of vision in the center of the visual field because of damage to the macula. Examples of macular degeneration include dry macular degeneration, wet macular degeneration, age-related macular degeneration, myopic macular degeneration, and idiopathic macular degeneration, and in one embodiment, age-related macular degeneration. Particularly, the composition, in one embodiment, includes significant inhibitory activity against photo-oxidation in age-related macular degeneration. In one embodiment, S-allyl-L-cysteine was found to protect cells from blue light-induced cell death in a dose dependent manner, as assayed in A2E-accumulated arising retinal pigment epithelia cell line (ARPE-19).

In one embodiment, the composition for the prevention or treatment of eye diseases may include S-allyl-L-cysteine in an amount of 5 to 99.9% by weight, and in another embodiment, in an amount of 5 to 60% by weight. In yet another embodiment, the S-allyl-L-cysteine composition not only protects ARPE-19 in a dose dependent manner to thus effectively prevent or treat eye disease, but also does not produce side effects.

In one embodiment, the composition for the prevention or treatment of eye disease may further include an anti-inflammatory agent or an anti-oxidant agent.

In one embodiment of the composition for the prevention or treatment of eye disease, the anti-inflammatory agent may be selected from the group consisting of ibuprofen, ketoprofen, flurbiprofen, fenoprofen, naproxen, piroxicam, tenoxicam, isoxicam, meloxicam, indomethacin, aceclofenac, diclofenac, and a combination thereof, and the anti-oxidant agent may be selected from the group consisting of vitamin A, vitamin C, vitamin E, carotenoid, zinc, copper, iron, manganese, lutein, zeaxanthin, selenium, glutathione (GSH), lycopene, and a combination thereof.

In one embodiment, S-allyl-L-cysteine may be obtained by isolation and purification from the plant *Allium* genus, by synthesis, or by fermentation. For example, S-allyl-L-cysteine may be prepared from *Allium* genus, such as garlic, elephant garlic, onion, scallion, etc., using the method disclosed in EP 0429080A1. Alternatively, S-allyl-L-cysteine may be synthesized or prepared using a technique known in the art, such as fermentation. Aside from direct preparation, S-allyl-L-cysteine may be commercially available.

According to one embodiment of the present invention, the composition for the prevention or treatment of eye disease may be prepared into a formulation selected from the group consisting of an oral dosage form, a mucosal application, an injection, an inhaler, and an external application.

In addition to one or more active ingredients, in one embodiment, the composition of the present invention may further include one or more inert, pharmaceutically acceptable vehicles. As typically applied to pharmaceutical preparations, any vehicle may be used in the present invention. Examples of the vehicle may include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propylhydroxybenzoate, talc, magnesium stearate, and mineral oil, without limitation. In addition, as yet another embodiment, the pharmaceutical composition of the present invention may further include a lubricant, a humectant, a sweetener, a flavor, an emulsifier, a suspending agent, and a preservative. For a detailed description of suitable pharmaceutically acceptable vehicles and formulations, reference may be made to Remington's Pharmaceutical Sciences ($19^{th}$ Ed., 1995).

Medicinal formulations may be administered to mammals such as rats, mice, livestock, humans, etc., via oral or non-oral routes, for example, orally, rectally, or intravenously, intramuscularly, subcutaneously, intrathecally or intra-cerebrovascularly. In one embodiment, a non-oral administration or transdermal administration may be used. In yet another embodiment, topical application by coating may be used.

The suitable dose of the medicinal formulation may vary depending on various factors including dosage forms, patient weight, age, gender and state of health, diet, the time of administration, the route of administration, the rate of excrement, and the response severity of patient. In one embodiment, the pharmaceutical composition of the present invention may be administered to an adult at a dose of 0.1-100 mg/kg once to several times per day for an oral dosage form, and applied to an adult at a dose of 1.0 to 3.0 ml one to five times a day for an external use agent for one month or longer. However, the dosage is without limitation.

In one embodiment, in a method that a person who has ordinary skill in the art can execute, the pharmaceutical composition may be formulated, together with a pharmaceutically acceptable vehicle and/or excipient into a unit dose form, or packed in multiple-dose containers. In this regard, the formulation may take any dosage form if it is suitable for pharmaceutical preparations, including oral forms such as powders, granules, tablets, capsules, suspensions, emulsions, syrups, and aerosols; external use applications such as ointments, creams, etc.; suppositories; and sterile injections. Lastly, in one embodiment, the pharmaceutical composition may further include a dispersant or a stabilizer.

In one embodiment, the active ingredient S-allyl-L-cysteine composition, that is both inhibitory of A2E accumulation in retinal pigment epithelial cells and suppressive of A2E oxidation, can exhibit excellent preventive and therapeutic effects on eye disease including age-related macular degeneration and degenerative retinal disease.

In addition, in one embodiment, the pharmaceutical composition of the present invention may be prepared as medicinal formulations effective for preventing or treating eye diseases.

Hereinafter, the present invention will be elucidated in detail by way of examples so that a person having ordinary skill in the art may carry out the present invention. However, the detailed descriptions of embodiments of the invention are not intended to be exhaustive or to limit the invention to the precise form disclosed above. While specific embodiments of, and examples for, the invention are described above for illustrative purposes, various equivalent modifications are possible within the scope of the invention, as recognized by those skilled in the relevant art.

Meanwhile, the symbol "%", as used throughout the specification to represent a concentration of a certain material, is intended to mean weight/weight (w/w) % for solid/solid, weight/volume (w/v) % for solid/liquid, and volume/volume (v/v) % for liquid/liquid, unless otherwise stated.

PREPARATION EXAMPLE

Cell Culture

The retinal pigment cell line used in experiments and analyses of the present invention arose from a retinal pigment epithelial cell line (ARPE-19: ATCC no. CRL-2302) purchased from the ATCC (American Type Culture Collection, Manassas Va.), and was maintained by passage as described in document (Sparrow, J. R. et al., A2E, alipofuscin fluorophore, in human retinal pigmented epithelial cells in culture. Invest Ophthalmol Vis Sci 1999, 40(12), 2988-95).

Briefly, the retinal pigment cell line was cultured in Dulbecco's modified Eagle's medium (DMEM, Gibco, USA) supplemented with antibiotics (Gibco, USA) including 100 U/ml penicillin, 100 mg/ml streptomycin, and amphotericin B, and 10% fetal bovine serum (Hyclone, USA) at 37° C. under 5% $CO_2$ conditions. The cells were allowed to adhere to the bottom of the culture plate, and cultured, with passage by treatment with a mixture of 1:4 trypsin:10% fetal bovine serum (Gibco, USA)-supplemented medium upon confluence.

For use in experiments, the cells were seeded at a density of $5\times10^4$ cells/well into 6-well plates.

Experimental Example 1

Suppressive Activity of S-Allyl-Cysteine Against Photo-Oxidation

Assay of S-Allyl-Cysteine for Suppressive Activity Against Blue Light-Induced Oxidation of A2E S-Allyl-cysteine was assayed for the ability to suppress the blue light-induced oxidation of A2E. First, 100 μM A2E was diluted to 20 μM in phosphate buffered saline (PBS), and 200 μl of the dilution was placed in each well of 96-well plates. Then, a negative control, a positive control (lutein 20 μM), or predetermined concentrations of S-allyl-cysteine (1, 10, 100 μM) were added to the dilution, and mixed by pipetting.

An LED lamp emitting blue light with a central wavelength of ca. 430 nm was operated above the microplates to induce photo-oxidation until the A2E absorbance was reduced by half. Absorbance was read on an ELISA before and after the induction of photo-oxidation. The measurements were applied to an A2E standard curve to obtain concentrations of A2E, and the difference in concentration before and after exposure to blue light was used to obtain the concentration of oxidized A2E. From the data, the inhibitory activity of the sample against A2E photo-oxidation was calculated according to the following Mathematical Formula 1. In Formula 1, Abs. means absorbance.

$$PI(\%) = \frac{A-B}{A} \times 100 \qquad \text{Mathematical Formula 1}$$

A=Abs. of A2E−Abs. of A2E+blue light
B={Abs. of A2E+sample)−Abs. of sample}−{(Abs. of A2E+sample+blue light)−(Abs. of sample−Abs. of sample+blue light)}

Experimental Example 2

Assay for Inhibitory Activity Against A2E Photo-Oxidation in Human Retinal Pigment Epithelial Cell Line (APRE-19)

Cytoprotective Activity of S-Allyl-Cysteine Against Blue Light-Induced Apoptosis of A2E-Accumulated Human Retinal Pigment Epithelial Cell Line CARPE-19)

Human retinal pigment cell line (ARPE-19) was seeded at a density of $5\times10^4$ cells/well into 96-well plates, and incubated with 20 μM A2E for 7 days to accumulate A2E. Then, the cells were treated with a negative control, a positive control (lutein: 20 μM), or predetermined concentrations of S-allyl-cysteine (1, 10, 100 μM) before exposure to blue light as described above.

Thereafter, cell viability was measured using 3-(4,5-dimethylthiazol-2-yl)-2,5-diphenyltetrazoliumbromide (MTT) assay. An MTT assay is a standard colorimetric assay for assessing cell viability, usually in a lab. Generally, viable cells are counted using a hemocytometer, or by measuring optical density; however, this method requires too much time and labor for large numbers of cells, and is apt to yield inaccurate results. As an alternative, the MTT assay is designed such that the yellow substrate tetrazolium MTT is reduced by metabolically active cells, in part by the action of mitochondrial dehydrogenase enzymes, into purple formazan that can be solubilized and quantified by spectrophotometric means. This assay can analyze the proliferation behavior of large numbers of cells rapidly and accurately. The purple solubilization solution in dimethyl sulfoxide (DMSO) shows a maximum optical density at 540 nm. Absorbance measurements at this wavelength exhibit a linear correlation with counts of viable cells. More viable cells produce a greater amount of formazan crystals, recoding higher absorbance.

According to the MTT assay (Sigma-Aldrich Inc., St. Louis, Mo., U.S.A.), DMEM containing 0.5 mg/ml MTT was added to each well and incubated at 37° C. for 2 hrs in an incubator under dark conditions. After completion of the reaction, cells in each well were sufficiently dissolved in 2 ml of DMSO (Sigma-Aldrich Inc.). Absorbance at 540 nm was read on an Enzyme-Linked Immunosorbent Assay (ELISA) microplate reader, and cell viability was expressed as percentage (%) to absorbance of the normal control, which did not accumulate A2E nor was treated with the samples.

Inhibitory Activity of S-Allyl-Cysteine Against Blue Light-Induced Oxidation of A2E In order to evaluate the inhibitory activity of S-allyl-L-cysteine against A2E photooxidation, concentrations of oxidized A2E were measured after exposure to blue radiation as described in Experimental Example 1, and the results are depicted in FIG. 1.

As can be seen in FIG. 1, the concentration of oxidized A2E was decreased by 20, 32, and 41% at 1, 10, and 100 µM of S-allyl-cysteine, respectively, compared to non-treated cells. Comparison with the lutein-treated group, the positive control, showed significant protective activity of the compound of the present invention. The data, taken together, demonstrated that S-allyl-L-cysteine inhibited the photooxidation of A2E in a dose-dependent manner.

Cytoprotective Activity of S-Allyl-Cysteine Against Blue Light-Induced Apoptosis of A2E-Accumulated ARPE-19

Figure 2:
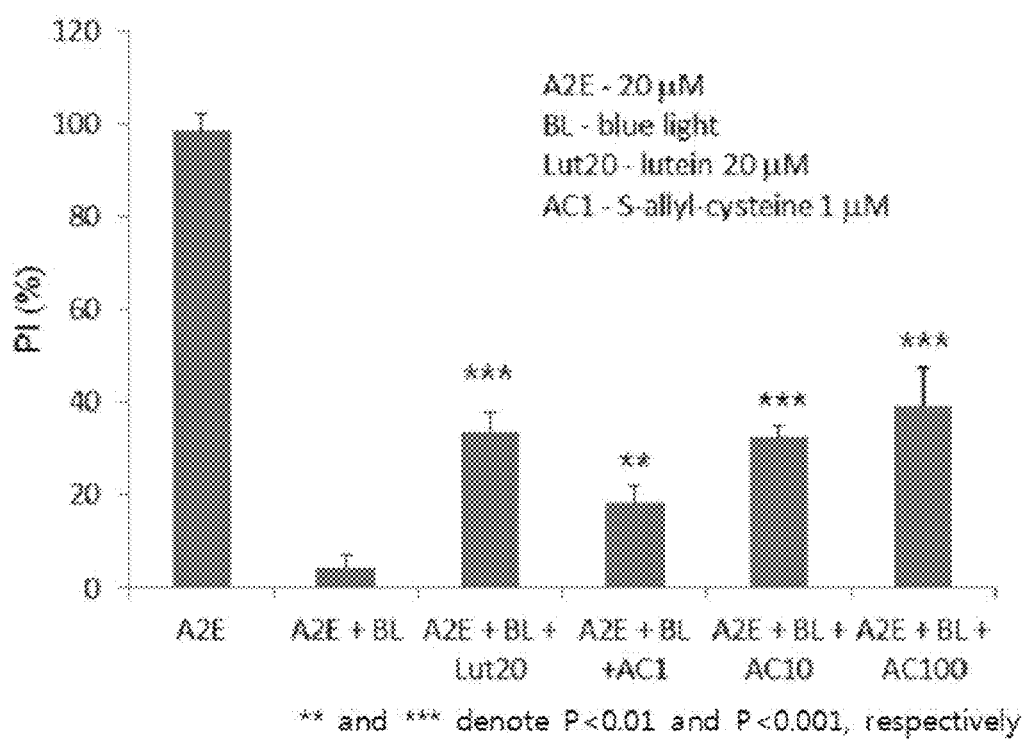
FIG. 2 is a graph showing the inhibitory activity of S-allyl-cysteine against the photo-oxidation of A2E in a human retinal pigment epithelial cell line (APRE-19).

In order to evaluate the cytoprotective activity of S-allyl-L-cysteine against blue light-induced apoptosis, an MTT assay was performed to measure cell viability as described in Experimental Example 2, and the results are depicted in FIG. 2.

As is apparent from FIG. 2, a significant difference in cell viability exists between the negative control exposed to blue light after A2E accumulation, and the positive control.

Cell viability was increased by 63, 134, and 167% when the cells were treated with 1, 10, and 100 µM of S-allyl-cysteine, respectively, compared to the negative control, demonstrating that S-allyl-L-cysteine protects human retinal pigment epithelial cells in a dose-dependent manner.

Although the disclosed embodiments of the present invention have been described for illustrative purposes, those skilled in the art will appreciate that various modifications, additions, and substitutions are possible, without departing from the scope and spirit of the invention as provided in the accompanying claims.

What is claimed is:

1. A method for treating eye disease, the method comprising:
    administering, to a subject, a composition comprised of S-allyl-L-cysteine, a pharmaceutically acceptable salt thereof, or a solvate or hydrate thereof as an active ingredient,
    wherein the eye disease is an age-related macular degeneration comprising wet age-related macular degeneration and dry age-related macular degeneration.

2. The method of claim 1, wherein the S-allyl-L-cysteine is used in an amount of 5 to 99.9% by weight, based on a total weight of the composition.

3. The method of claim 1, wherein the S-allyl-L-cysteine is obtained by isolation and purification from a plant of *Allium* genus, by synthesis, or by fermentation.

4. The method of claim 1, wherein the composition further comprises an anti-oxidant agent.

5. The method of claim 1, wherein the composition further comprises an anti-inflammatory agent.

6. The method of claim 5, wherein the anti-inflammatory agent is selected from the group consisting of ibuprofen, ketoprofen, flurbiprofen, feno-profen, naproxen, piroxicam, tenoxicam, isoxicam, melo-xicam, indomethacin, aceclofenac, and diclofenac, and a combination thereof.

7. The method of claim 1, wherein the composition is included in a medicinal formulation, and the medicinal formulation is selected from the group consisting of an oral dosage form, a mucosal application, an injection, an inhaler, and an external application.

8. The method of claim 4, wherein the anti-oxidant agent is selected from the group consisting of vitamin A, vitamin C, vitamin E, carotenoid, zinc, copper, iron, manganese, lutein, zeaxanthin, selenium, glutathione (GHS), lycopene, and a combination thereof.

* * * * *